United States Patent [19]

Dittmar et al.

[11] Patent Number: 4,841,543
[45] Date of Patent: Jun. 20, 1989

[54] PROBE FOR MEASURING THE THERMAL CONDUCTIVITY OF MATERIALS

[75] Inventors: André Dittmar; Georges Delhomme; Bernard Roussel; Joseph Chatonnet, all of Lyons, France

[73] Assignee: Centre National De La Recherche Scientifique (C.N.R.S.), Paris, France

[21] Appl. No.: 920,241

[22] Filed: Oct. 17, 1986

[30] Foreign Application Priority Data

Oct. 23, 1985 [FR] France ................... 8515932

[51] Int. Cl.⁴ ........................... G01N 25/18
[52] U.S. Cl. ................................ 374/44
[58] Field of Search ............. 374/29, 43, 44, 35, 374/164, 208; 73/154; 128/632, 634, 664, 691, 734, 736, 742; 136/227, 229, 230, 232

[56] References Cited

U.S. PATENT DOCUMENTS

| 3,256,734 | 6/1966 | Storke, Jr. ............... | 374/43 |
| 4,541,730 | 9/1985 | Comey et al. .............. | 374/43 |
| 4,705,498 | 11/1987 | Goss ....................... | 604/6 |
| 4,733,055 | 3/1988 | Cunningham ................ | 219/540 |

FOREIGN PATENT DOCUMENTS

| 1087752 | 8/1960 | Fed. Rep. of Germany ...... | 128/736 |
| 2389128 | 12/1978 | France .................... | 128/742 |
| 805154 | 2/1981 | U.S.S.R. .................. | 374/43 |
| 1319865 | 6/1973 | United Kingdom ........... | 374/164 |

OTHER PUBLICATIONS

Challoner, A. V. J., "Accurate Measurement of Skin Blood Flow by a Thermal Conductance Method", *Medical & Biological Engineering*, vol. 13, No. 2, pp. 196-201, Mar. 1975.

Qiao et al, "Simultaneous Measurement of Electrical Admittance...", *Med. & Biol. Eng. & Comput.*, vol. 25, pp. 299-304, May 1987.

*Primary Examiner*—William A. Cuchlinski, Jr.
*Assistant Examiner*—W. Morris Worth
*Attorney, Agent, or Firm*—Weingarten, Schurgin, Gagnebin & Hayes

[57] ABSTRACT

This invention relates to the measurement of thermal conductivity. The measuring probe according to the invention is characterized in that it comprises:

a plate defining, on its face of application, areas located on the same plane, occupied by the measurement zones ($Z_1$, $Z_2$) which are constituted by conducting segments connected in series from one zone to the other by thermocouples, a plane heating element placed, outside the face of application, in relation with the median zone $Z_1$, a coating made of electrically insulating matter, covering the measurement zones $Z_1$, $Z_2$, a cover made of insulating matter covering the plate, and a mass (M) of heat-insulating matter occupying the volume defined by the plate and the cover. The invention is more particularly applicable to the study of the thermal conductivity of biological tissues.

12 Claims, 3 Drawing Sheets

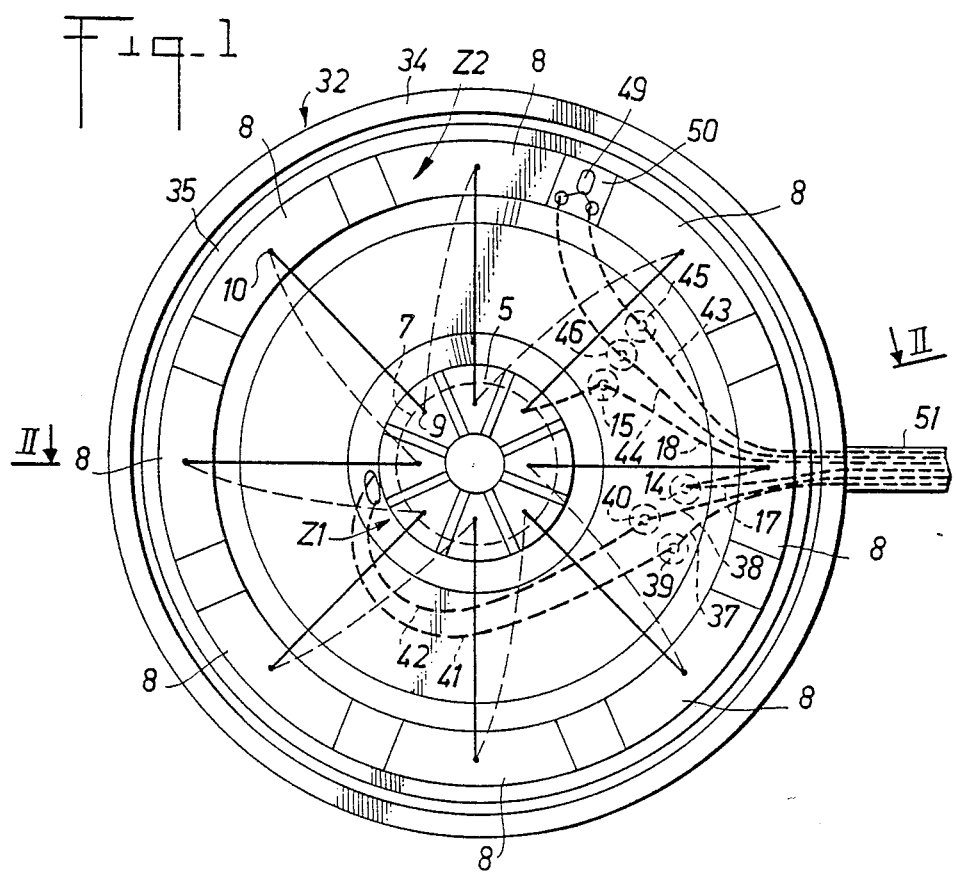
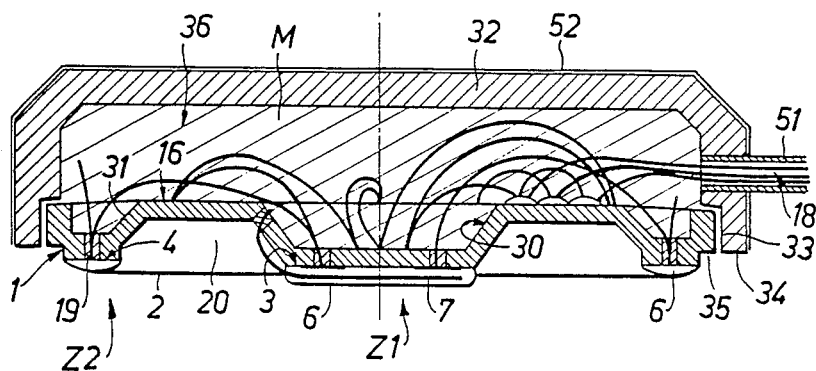

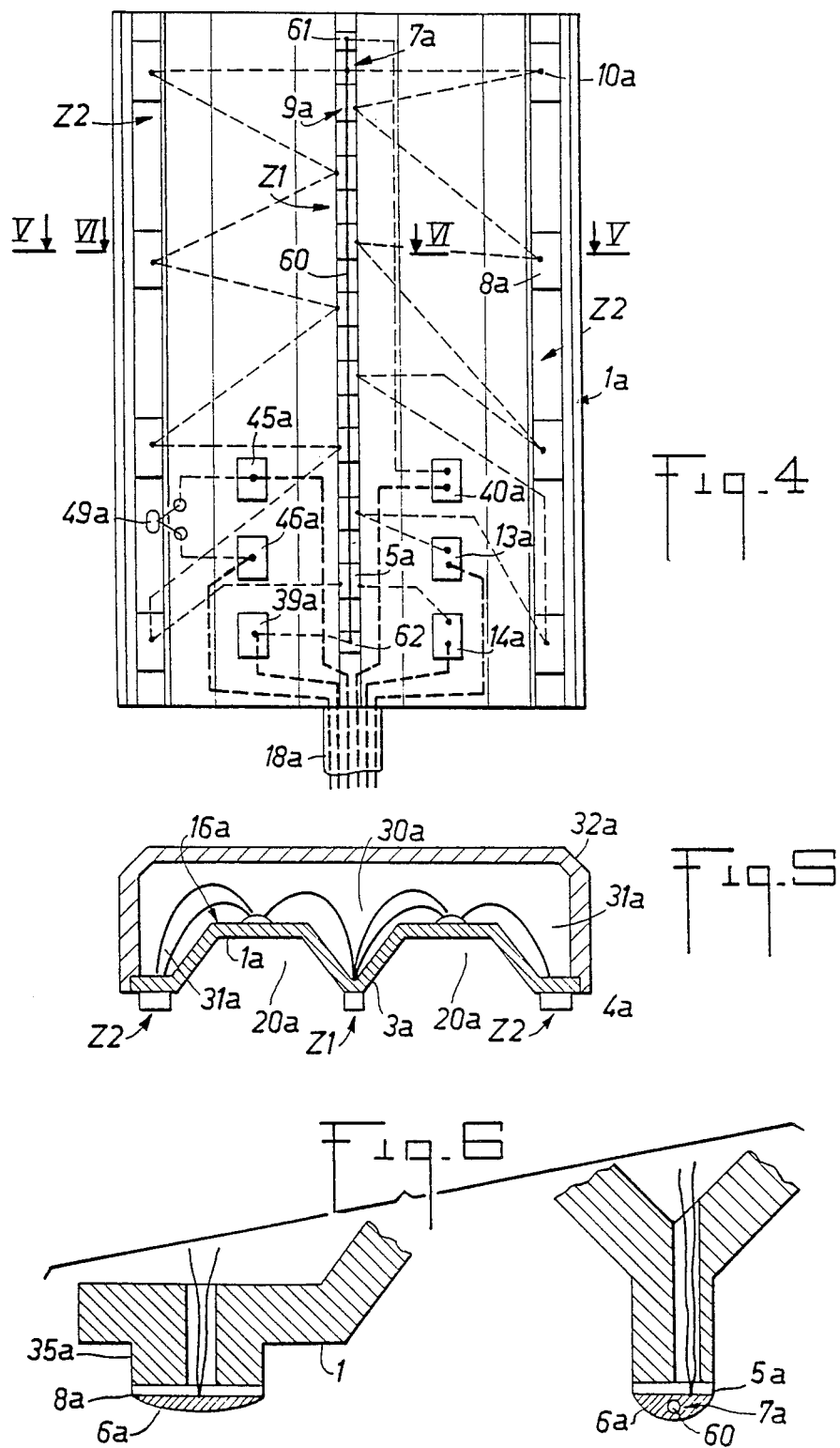

PROBE FOR MEASURING THE THERMAL CONDUCTIVITY OF MATERIALS

The present invention relates to the measurement of thermal conductivity of materials for the purpose of characterizing them.

The measurement of thermal conductivity is employed in numerous applications, for example:

the study of thermo-regulation of living tissues in medical application;

the study of the nature of biological tissues and in particular the content of lipids, proteins or the assessment of degrees of burn or of necrosis;

the study of the water content;

the study of the blood flow in the tissues;

the study of the characterization of nonbiological materials from their thermal conductivity.

The conventional technique of measuring thermal conductivity raises problems, as a sample of imposed geometrical form of a material to be analyzed must be made available. This sample is placed in an enclosure between two plates taken to different temperatures and which clamp it in the manner of a press. The conductivity is measured from the difference in temperature of the plates and the heat flow passing through the sample between the plates.

This modus operandi is restricting and slow and, in addition, is inapplicable in situ and in vivo.

In order to reduce such constraints, the prior technique also proposed employing an apparatus comprising a reference measurement zone, assessing the surface temperature of the material and a measurement zone associated with a heating element. The principle consists in supplying energy by the heating element, so as to establish a determined constant difference in temperature between the two zones. The thermal conductivity may be assessed by taking into account the energy spent for maintaining this determined temperature difference.

Among the publications envisaging such a technique, particular mention may be made of the journal MEDICAL AND BIOLOGICAL ENGINEERING, March 1975, page 196. According to this publication, an apparatus for measuring the thermal conductivity employs, on a plane face of a mass of plastics material, a ring of copper disposed concentrically to a central disc likewise made of copper. These two conducting metal elements constitute, respectively, the outer reference measurement zone and the zone of measurement of the heated surface. To that end, the central disc is associated, inside the coating of plastics material, with a heater coil. The conductors, connected to the copper elements and to the heating element, are embedded in the mass of plastics material and connected to a power cord. The link between the outer ring and the copper disc is ensured by a succession of junctions in series making it possible to measure the difference between the sum of the electromotive forces of the peripheral junctions and the sum of the electro-motive forces of the central junctions.

Such an apparatus is not satisfactory, as it does not take into account the essential elements which must be considered in such a domain of application.

In fact, the measurement of the thermal conductivity of materials or biological tissues requires that very slight thermal variations, of the order of 1%, be assessed. It is therefore important to be able:

to limit the inertia of the measuring apparatus in order to obtain good rapidity and high precision;

to limit the conductivity between the zone of heat supply and the reference measurement zone, in order to avoid influencing the latter by the transfer of calories within the measuring apparatus;

to limit the heat resistance between the point of measurement and the contact surface of the medium to be characterized, in order to ensure a rapid heat transfer between measurement medium, heating element and temperature measuring element;

to limit the thermal inertia of the heating means, so as to obtain a rapid release of the energy supply;

to have available the lowest axial heat resistance of the heating means, but, on the contrary, the highest resistance perpendicularly to this axis;

to assess every measurement of temperature precisely, in order to have high sensitivity.

The apparatus as proposed in the prior art publication mentioned above does not respond to the above objectives by reason of the construction recommended.

Firstly, the heating element is constituted by a coil which presents a high inertia. In addition to its dimensions, this coil is disposed in relation with the rear face of the central conducting disc and consequently the resistance of the latter will disturb the transmission of the energy supply.

The central disc and the ring are disposed in proximity relation in the same plane, within the same matter, so that an internal transfer of calories influences the measurement of the peripheral zone.

The heat transfer and measurement means are included in a mass of the same matter which undergoes a heating transmitted to the other different constituent elements and consequently disturbing the differential measurement between the heated zone and the non-heated reference zone.

It is an object of the present invention to overcome the drawbacks associated with such a solution, by proposing a novel probe for measuring the thermal conductivity, which is of simple design, robust, of small dimensions, presenting characteristics of measurement which are precise, sensitive, stable, rapid and reproducible.

In order to attain the objectives set forth hereinabove, the probe forming the subject matter of the invention is characterized in that it comprises:

a plate made of electrically and thermally insulating material shaped so as to define, on its face of application, areas located on the same plane, separated by depressions and occupied by the measurement zones ($Z_1$, $Z_2$) which are constituted by heat-conducting segments separated from one another but connected in series successively from one zone to the other by thermocouples of which the hot junctions are borne by the sectors of the median zone $Z_1$ and the cold junctions are borne by the sectors of zone $Z_2$, a plane heating element placed, outside the face of application, in relation with the median zone $Z_1$, a coating made of electrically insulating matter laden with heat-conducting particles, covering the measurement zones $Z_1$, $Z_2$, a cover made of electrically and thermally insulating matter covering that face of the plate occupied by the conductors, and a mass (M) of heat-insulating matter occupying the volume defined by the plate and the cover.

The invention will be more readily understood on reading the following description with reference to the accompanying drawings, in which:

FIG. 1 is a plan view of an embodiment of the probe according to the invention.

FIG. 3 is an exploded view in perspective showing more clearly a constructive feature of the object of the invention.

FIG. 4 is a plan view of a second embodiment of the object of the invention.

FIG. 5 is a transverse section taken along line V—V of FIG. 4.

FIG. 6 is a partial transverse section taken, on a larger scale, along line VI—VI of FIG. 4.

Figure 2:
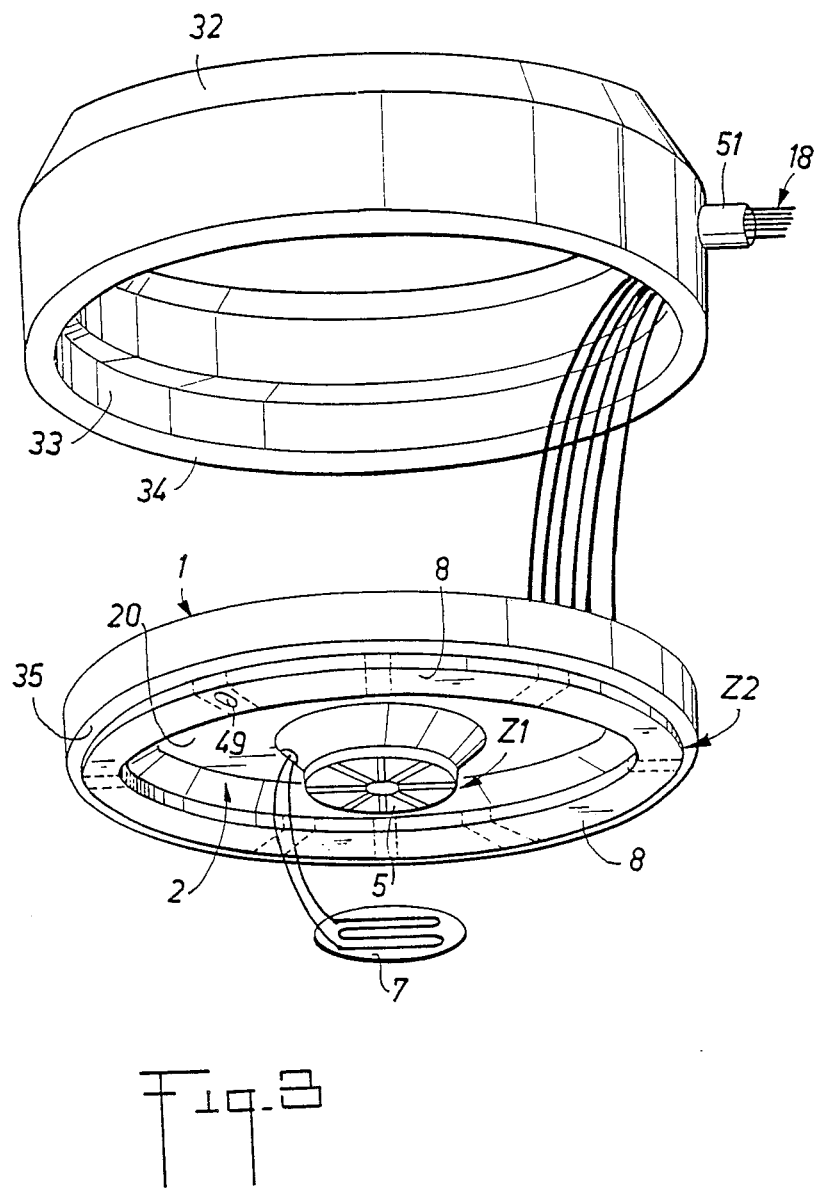
FIG. 2 is an elevational section taken substantially along line II—II of FIG. 1.

Referring now to the drawings, and in accordance with the first embodiment illustrated in FIGS. 1 to 3, the probe for measuring the thermal conductivity of materials comprises a plate 1 made of a resistant plastics material, which may be moulded or machined. By way of example, the plate 1 may be made of an epoxy resin including a filler of glass fibers. In the example illustrated, the probe is generally cylindrical in form and comprises a circular plate 1.

Plate 1 comprises, on its so-called face 2 of application, two plane areas 3 and 4 disposed in a common plane. Area 3 is of circular form and occupies the centre of plate 1, whilst area 4 is of annular form, being concentric to area 3 and occupying that part close to the peripheral edge of plate 1.

Area 3 presents on its surface heat-conducting segments 5 which are for example constituted by deposits of copper or silver. Segments 5 present the form of angular sectors and are separated from one another. The assembly formed by segments 5 is covered by a layer 6 of electrically insulating matter, in particular a resin, including particles of matter such as aluminium which increase the thermal conductivity without being detrimental to the electrical insulation. This layer 6 covers a plane heating element 7 which is constituted by a circuit with constant resistance formed for example by a strain gauge made of constantan or by a deposit of a thin resistive layer. The heating element 7 is thus disposed outside the face of application 2, being separated from segments 5 by a very small thickness of layer 6. Segments 5 constitute a zone $Z_1$ for measuring the temperature of the heated zone of the material.

The annular area 4 presents on its surface heat-conducting segments 8 made of the same matter as segments 5, in a number identical thereto to which they correspond radially. The segments 8 of area 4, likewise covered with a layer 6, constitute an outer zone $Z_2$ for measuring the reference temperature of the material.

Zones $Z_1$ and $Z_2$ are connected together by thermocouples in series comprising hot junctions 9 on segments 5 and cold junctions 10 on segments 8. The wires for connecting the junctions are of small diameter, preferably less than 0.1 mm in order to reduce the parasitic heat conduction. The connecting wires are fixed by welding on the outer faces of segments 5 and 8 and pass through plate 1 via holes 19 which are then stopped with resin such as an epoxy resin. The two end segments of the series of junctions are connected by two wires to two connection discs 14 and 15 added on the face 16 of the plate opposite the face of application and referred to hereinafter as internal. Discs 14 and 15 serve for the connection of two conductors 17 and 18 forming part of a cord 18 for connection to a servo-control and measuring apparatus.

Plate 1 is shaped so that zones $Z_1$ and $Z_2$ are separated by an annular depression or hollow 20, so that the surface of application of face 2 is limited to areas 3 and 4. This is provided to limit the conduction between the two measurement zones $Z_1$ and $Z_2$ when the apparatus is in operation after application on the material or tissue.

The shape of plate 1 is also chosen to define, from the internal face 16 and in register with areas 3 and 4, a central internal depression or hollow 30 and an annular depression or hollow 31. Such shape makes it possible to limit the thickness of matter of the plate at the level of zones $Z_1$ and $Z_2$ and thus to reduce the thermal inertia by reducing the calorific energy capable of being absorbed.

FIG. 1 shows that plate 1 presents a substantially constant thickness but, in certain cases, it may be envisaged further to reduce the thickness of matter comprised in zones $Z_1$ and $Z_2$ so as further to limit the internal thermal conduction between the central and peripheral zones.

Plate 1 is associated with a cover 32 made in the same matter and which is hermetically fitted by a bearing surface 33 on the peripheral edge of plate 1. Edge 34 of cover 32 is recessed with respect to the plane of the face of application 2 and is established, for example, in the plane of the bottom of a peripheral rabbet 35 formed in face 2 of the plate outside area 4. Cover 32 defines with plate 1 a volume 36 occupied by a mass M of heat-insulating material, for example expanded polystyrene, in which are embedded the interjunction connecting conductors, conductors 13, 14, 17 and 18, as well as two so-called electrical connection conductors 37 and 38, connected to two connection discs 39 and 40 on which are connected two conductors 41 and 42 leading to the plane heating element 7.

The supply conductors 37 and 38 form part of cord 18 which may, if necessary, also comprise two conductors 43 and 44 connected to two discs 45 and 46 from which are also connected two conductors 47 and 48 leading to a probe 49 for measuring temperature, such as a thermistor. Probe 49 is placed in the reference measurement zone $Z_2$, being disposed in a housing 50 formed by plate 1 in a gap between two successive segments 8.

Cord 18, constituted by all the conductors, passes through cover 32 in a protective sheath 51.

The probe described hereinabove constitutes a measuring element of very small dimensions, made in robust manner, being given that the fragile constituent elements, such as the wires connecting the junctions in series, are embedded and protected inside the mass M of heat-insulating matter occupying volume 35.

Such a measuring probe is put to use by applying the face of application 2 on the surface of the material or tissue to be analyzed, in order to measure the temperature of this surface via the segments 8 of zone $Z_2$. The heating element 7 is then fed with current so as to supply thermal energy to the measurement zone $Z_1$. The sum of the electro-motive forces of the peripheral junctions in series between zones $Z_1$ and $Z_2$ is measured so as to assess the difference in temperature between the two zones $Z_1$ and $Z_2$. This measurement makes it possible to adjust the supply of energy to zone $Z_2$ in order to maintain constant a determined temperature difference between zones $Z_1$ and $Z_2$. Measurement of the energy supplied enables the thermal conductivity of the material or tissue to be assessed.

The structure of the probe according to the invention is particularly selected, as seen from the foregoing, so as to reduce the thermal bridges between the peripheral reference zone $Z_2$ and the central heated zone $Z_1$. Such reduction is obtained by the shape of the plate 1 and, more particularly, by the presence of the annular hollow 20 separating areas 3 and 4 and by rabbet 35.

Depressions or hollows 30 and 31 are also provided to reduce the thermal absorption from segments 5 and 8 and thus to obtain a high response speed and a high sensitivity of measurement.

The existence of connecting discs 14, 15, 39, 40 and 45, 46 makes it possible to use connecting or supply conductors of normal section on which the stresses of mechanical use are generally applied. This concept makes it possible to employ, from the discs, interjunction connecting conductors of very small section which present the advantage of reducing the parasitic thermal conduction.

With a view to limiting the thermal influence which the infra-red radiations might for example have on the measurement zones $Z_1$ and $Z_2$, cover 32 is provided, at least on its outer face, with a coating 52 reflecting the infra-red radiations. Such a coating may also be provided on the inner face of cover 32 for the same purpose.

FIGS. 4 to 6 illustrate a variant embodiment in which the probe is produced so as to present a zone $Z_1$ of linear type, occupying the longitudinal median part of a plate 1a of which the longitudinal edges are occupied by two reference measurement zone $Z_2$ extending parallel, on either side and equidistant from zone $Z_1$. Plate 1a is shaped similarly to what is described hereinabove, so as to comprise two depressions or hollows 20a separating the areas 3a and 4a occupied by zones $Z_1$ and $Z_2$. The plate also defines, from the inner face 16a, depressions or hollows 30a and 31a. Hollows 20a are open at the transverse ends of plate 1a so as to be able to constitute in addition tunnels for circulation of the ambient medium, avoiding the creation of a medium in confinement between the measurement and reference zones; which confinement would be responsible for a modification of the percentage of humidity of the material to be characterized.

Zone $Z_1$ comprises conducting segments 5a whose number is equal to the sum of sectors 8a distributed in the two outer lateral zones $Z_2$. FIG. 4 shows the series junction diagram retained between the conductor segments 5a and 8a, employing wires of small section connecting the hot junctions 9a to the cold junctions 10a.

In this embodiment, the plane heating element 7a is constituted by a wire 60 of small section, extending linearly opposite all the conducting segments 5a, being stretched between two connecting terminals 61 and 62. Wire 60, embedded and maintained in layer 6a, is for example constituted by a wire electrically resistant independently of the temperature or of very low coefficient of temperature, made for example of constantan.

The same advantages as hereinabove are offered by this variant embodiment.

The invention is not limited to the embodiments described and shown, as various modifications may be made thereto without departing from its scope.

What is claimed is:

1. A probe for measuring the thermal conductivity of materials, comprising:
   a support plate made of electrically and thermally insulating matter and having a surface defining a face of application thereby said support plate has on said surface defining said face of application a median conducting measurement zone (Z1) divided into a first plurality of heat conducting sections and at one reference measurement zone (Z2) divided into a second plurality of heat conducting sections, and whereby said median con measurement zone (Z1) is separated from said reference measurement zone (Z2) by at least one depression in said surface of said support plate defining said face of application so as to limit the thickness of said support plate in an area between said median conducting measurement zone (Z1) and said reference measurement zone (Z2) thereby reducing thermal conduction through the face of the probe;
   a plurality of thermocouples comprised of interjunction connecting conductors and disposed on a portion of said support plate on said surface defining said face of application, each thermocouple having at least one hot junction and at least one cold junction, wherein said thermocouples connect said first plurality of sections of said median conducting measurement zone (Z1) and said second plurality of sections of said reference measurement zone (Z2) in series, and wherein said hot junctions are disposed on said first plurality of sections and said cold junctions are disposed on said second plurality of sections;
   a heating element of planar shape disposed on said support plate at said median conducting measurement zone (Z1) and laterally offset from a plane corresponding to said face of application;
   a coating of electrically insulating matter having heat conducting particles and disposed on said median conducting measurement zone (Z1) with said heating element and on said reference measurement zone (Z2);
   a plurality of conductors disposed on said surface of said support plate opposite to said surface defining said face of application and connecting said heating element and said thermocouples to external driving circuitry; and
   a covering of electrically and thermally insulating matter disposed on said surface of said support plate opposite to said surface defining said face of application and enclosing said plurality of thermocouples and said plurality of said conductors.

2. The measurement probe of claim 1, wherein said covering of electrically and thermally insulating matter is comprised of a discrete cover of electrically and thermally insulating matter enclosing said plurality of thermocouples and said plurality of said conductors in a volume and wherein said volume is filled with a mass of heat-insulating matter.

3. The measurement probe of claim 1, wherein said support plate has at least one depression in said surface opposite to said surface defining said face of application so as to limit the thickness of said support plate.

4. The measurement probe of claim 1 wherein said interjunction connecting conductors are of small diameter.

5. The measurement probe of claim 1, further comprising a plurality of contact disks exposed on said surface of said support plate opposite to said surface defining said face of application, and wherein said contact disks connect said plurality of conductors to said heating element and said thermocouples.

6. The measurement probe of claim 1, wherein said covering is comprised of a discrete cover of electrically and thermally insulating matter and wherein a seal is fitted between said cover and said support plate in a recess in said cover and a peripheral edge of said support plate on said face of application.

7. The measurement probe of claim 1, wherein said covering further includes a coating of infrared reflecting matter.

8. The measurement probe of claim 1, wherein said median conducting measurement zone (Z1) is circular and said reference measurement zone (Z2) annular and concentric to said circular median conducting measurement zone (Z1).

9. The measurement probe of claim 1, wherein said median conducting measurement zone (Z1) is linear and wherein said probe has two reference measurement zones (Z2) laterally and equidistantly spaced parallel from said median conducting measurement zone (Z1).

10. The measurement probe of claim 1, wherein a temperature measuring probe is disposed on said support plate in a space between two of said second plurality of sections of the said reference measurement zone (Z2).

11. A probe for measuring the thermal conductivity of materials, comprising:
a support plate made of electrically and thermally insulating matter and having a surface defining a face of application, whereby said support plate has on said surface defining said face of application a median conducting measurement zone (Z1) divided into a first plurality of heat conducting sections and at one reference measurement zone (Z2) divided into a second plurality of heat conducting sections, and whereby said median conduction measurement zone (Z1) is separated from said reference measurement zone (Z2) by at least one depression in said surface in the said support plate defining said face of application so as to limit the thickness of said support plate in an area between said median conducting zone (Z2) thereby reducing thermal conduction through of the probe;
a plurality of thermocouples comprised of interjunction connecting conductors and disposed on said surface of said support plate defining said face of application, each thermocouple having at least one hot junction and at least one cold junction, wherein said thermocouples connect said first plurality of segments of said median conducting measurement zone (Z1) and said second plurality of sections of said reference measurement zone (Z2) in series, and wherein said hot junctions are disposed on said first plurality of sections and said cold junctions are disposed on said second plurality of sections;
a heating element disposed on said support plate at said median conducting measurement zone (Z1); and
a plurality of conductors disposed on said surface of said support plate opposite to said surface defining said face of application and connecting said heating element and said thermocouples to external driving circuitry.

12. A probe for measuring the thermal conductivity of materials, comprising:
a support plate made of electrically and thermally insulating matter and having a surface defining a face of application whereby said support plate has on said surface defining said face of application a median conducting measurement zone (Z1) divided into a first plurality of heat conducting sections and at one reference measurement zone (Z2) divided into a second plurality of heat conducting sections;
a plurality of thermocouples comprised of interjunction connecting conductors and disposed on said surface of said support plate defining said face of application, each thermocouple having at least one hot junction and at least one cold junction, wherein said thermocouples connect said first plurality of sections of said median conducting measurement zone (Z1) and said second plurality of sections of said reference measurement zone (Z2) in series and wherein said hot junctions are disposed on said first plurality of sections and said cold junctions are disposed on said second plurality of sections;
a heating element disposed on said support plate at said median conducting measurement zone (Z1);
a coating of electrically insulating matter having heat conducting particles and disposed on said median conducting measurement zone (Z1) with said heating element and on said reference measurement zone (Z2); and
a plurality of conductors disposed on said surface of said support plate opposite to said surface defining said face of application and connecting said heating element and said thermocouples to external driving circuitry.

* * * * *

UNITED STATES PATENT AND TRADEMARK OFFICE
CERTIFICATE OF CORRECTION

PATENT NO. : 4,841,543

DATED : June 20, 1989

INVENTOR(S) : Andre Dittmar; Bernard Roussel; Georges Delhomee; Joseph Chatonnet It is certified that error appears in the above-identified patent and that said Letters Patent is hereby corrected as shown below:

In Column 3, line 32, "surface heat-conducting" should read --surface $\underline{n}$ heat-conducting--

In Column 6, line 1, "thereby" should read --whereby--.

In Column 6, line 7, "con" should read --conducting--.

In Column 7, line 35, "conduction" should read --conducting--.

In Column 7, line 41, "median conducting zone (Z2)" should read --median conducting measurement zone (Z1) and said reference measurement zone (Z2)--.

In Column 7, line 42, "through of the" should read --through the face of the--.

In Column 8, line 22, "at one" should read --at least one--.

Signed and Sealed this

Thirtieth Day of June, 1992

*Attest:*

DOUGLAS B. COMER

*Attesting Officer*     *Acting Commissioner of Patents and Trademarks*